United States Patent
Leung et al.

(10) Patent No.: US 8,617,484 B1
(45) Date of Patent: Dec. 31, 2013

(54) IODINE-DISPENSING ANTIFOULANT IMPLEMENTED WITH DISPENSING SHUTTER

(75) Inventors: Kimberly Leung, San Diego, CA (US); Charles Ringer, San Diego, CA (US)

(73) Assignee: The United States of America as represented by the Secretary of the Navy, Washington, DC (US)

(*) Notice: Subject to any disclaimer, the term of this patent is extended or adjusted under 35 U.S.C. 154(b) by 720 days.

(21) Appl. No.: 12/749,850

(22) Filed: Mar. 30, 2010

(51) Int. Cl.
*A61L 2/00* (2006.01)
*G07F 11/00* (2006.01)

(52) U.S. Cl.
USPC ............. 422/301; 422/292; 73/53.01; 221/12

(58) Field of Classification Search
USPC .................. 422/1, 6, 28, 105, 119, 292, 301; 210/748.16, 749; 73/1.02, 32 R, 53.01; 307/413; 134/6, 22.17, 22.19; 221/12
See application file for complete search history.

(56) References Cited

U.S. PATENT DOCUMENTS

| | | |
|---|---|---|
| 4,065,387 A | 12/1977 | Tsuneki et al. |
| 5,176,836 A | 1/1993 | Sauer et al. |
| 5,772,971 A | 6/1998 | Murphy et al. |
| 2009/0041621 A1* | 2/2009 | Kelly et al. ............... 422/40 |

OTHER PUBLICATIONS

Teledyne RD Instruments; Citadel CTD-NH Product Specification; believed to have been available online starting Apr. 2010 at http://www.rdinstruments.com/citadel.aspx.

Derek V. Manov, Grace C. Chang, and Tommy D. Dickey Methods for Reducing Biofouling of Moored Optical Sensors Journal of Atmospheric and Oceanic Technology vol. 21, pp. 958-968 (2004, American Meteorological Society).

* cited by examiner

*Primary Examiner* — Monzer Chorbaji
(74) *Attorney, Agent, or Firm* — Kyle Eppele; J. Eric Anderson

(57) ABSTRACT

Sensors, such as optical sensors and other sensors used in an aqueous environment are protected from biological contamination by applying a biocide behind a shutter. The shutter is capable of covering a subject portion of the sensor or surrounding mounting surface adjacent the sensor in at least a semi-sealing manner. A well or reservoir forms a chamber in the shutter that is capable of holding a biocide having a limited water solubility and a low environmental toxicity in the aqueous environment, for example, anhydrous iodine crystals. The reservoir is in communication with the portion of the sensor while positioned against the portion of the sensor or surrounding mounting surface adjacent the sensor.

7 Claims, 3 Drawing Sheets

IODINE-DISPENSING ANTIFOULANT IMPLEMENTED WITH DISPENSING SHUTTER

FEDERALLY-SPONSORED RESEARCH AND DEVELOPMENT

This invention is assigned to the United States Government. Licensing inquiries may be directed to Office of Research and Technical Applications, Space and Naval Warfare Systems Center, Pacific, Code 72120, San Diego, Calif., 92152; telephone 619-553-2778; email: T2@spawar.navy.mil. Reference Navy Case No. 100021.

BACKGROUND

The disclosed techniques relate to preventing or retarding biofouling of waterborne sensors such as optical lenses.

SUMMARY

Protection of a sensor in an aqueous environment is achieved by providing a shutter having a facing surface and a reservoir, the shutter being configured to cover a mating surface of the sensor or surrounding mounting surface in at least a semi-sealing manner. The reservoir is provided in the shutter and is capable of holding a biocide having a limited water solubility and a low environmental toxicity in the aqueous environment. The reservoir is in communication with the mating surface while positioned against the mating surface.

DETAILED DESCRIPTION

Figure 1:
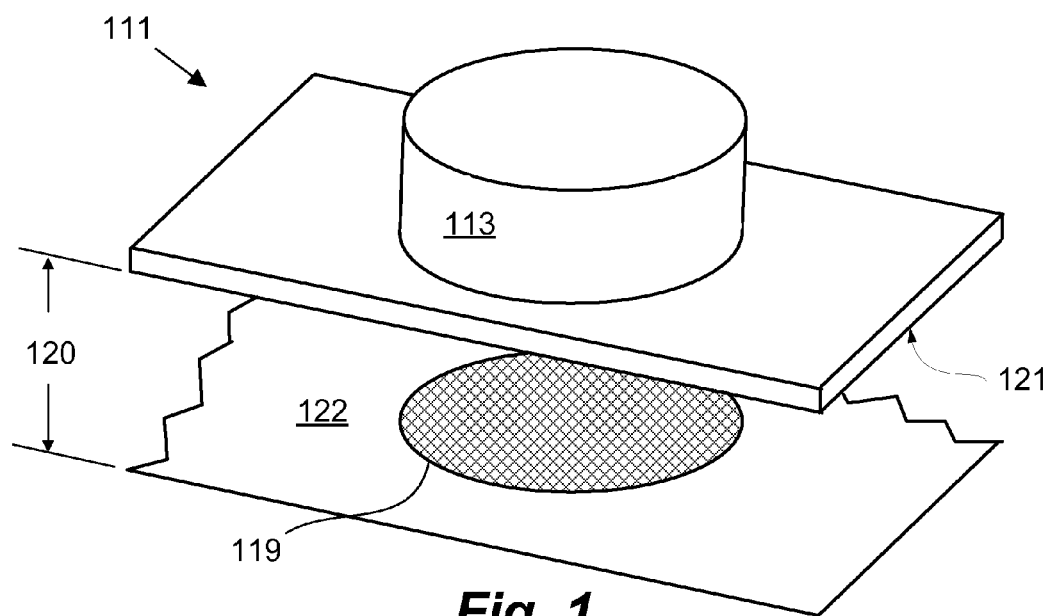
FIG. 1 is a front view of a shutter used for holding a biocide.

This disclosure describes providing a biocide delivery technique for preventing biofouling on marine sensors, with intermittent, long-term use. Such sensors include optical sensors and other sensors exposed to the aquatic environment.

Moored optical instruments in the ocean are highly susceptible to biofouling, a buildup of micro- and macro-organisms that cover the optical surface and limit the length of time an instrument is useful. As sensors are increasingly designed to be used for a year or more, it is crucial to find better methods of keeping the sensors clean from fouling, as these devices need substantially unobstructed light paths.

Visible biofouling usually consists of organisms such as barnacles, tubeworms, algae, etc. colonizing on the surface of the sensor; however, long before these organisms colonize a surface, two other layers must be established. On contact with sea water, a surface immediately acquires a protein layer, which in turn attracts a layer of marine bacteria. This bacteria layer provides an appropriate surface for the larvae of macroorganisms to settle.

Current methods of preventing biofouling of instruments include copper shutters, wipers/scrubbers, various biocides, anti-fouling paint, and UV LEDs. All have shown some benefit, but also have limitations for application to optical sensors and similar sensors which are intended to be exposed to the aquatic environment. In previous experiments, the use of copper shutters in an attempt to prevent biofouling resulted in a clear jelly-like precipitate between the shutter and sensor, which would inhibit light sensing. Wipers and scrubbers require large amounts of power to run regularly, which is difficult to achieve when leaving an instrument to run autonomously for long periods. Biocides have been shown to work in closed systems, but there is a lack of delivery method for systems where the sensor is exposed to the ocean environments. Anti-fouling paint has also been shown to be effective, but cannot be used on optical sensors and similar sensors which are intended to be exposed to the aquatic environment, as the surface must remain clear for light sensing. UV LEDs present an attractive option, as there are no moving parts and the application of UV effectively reduces fouling, but power requirements can again be prohibitive.

The technique may comprise the use of anhydrous iodine crystals and a plastic shutter to cover the sensor. The shutter includes a well to capture the iodine crystals. The iodine acts as the biocide, and the shutter acts as the delivery mechanism. Iodine is a known disinfectant, commonly used in low concentrations for water purification. When used in its crystalline form, the iodine dissolves to saturation in the presence of water, and the remainders of the crystals remain solid. The shutter may be perforated on its underside (the side adjacent to the sensor), allowing the crystals to remain captive, while water trapped in the space between the shutter and the sensor becomes saturated with the iodine.

The disclosed technique uses iodine as a biocide, and a shutter enclosing the sensor as a delivery system. Shutters have the advantage of shielding the sensor from both light (and thus photosynthesis) and a constant flow of salt water. However, this alone will not prevent fouling. The delivery of a biocide enhances the resistance to fouling, and the immediate and constant application inhibits the initial biofilm from forming, and therefore prevents the usual growth of micro- and macroorganisms.

Figure 2:
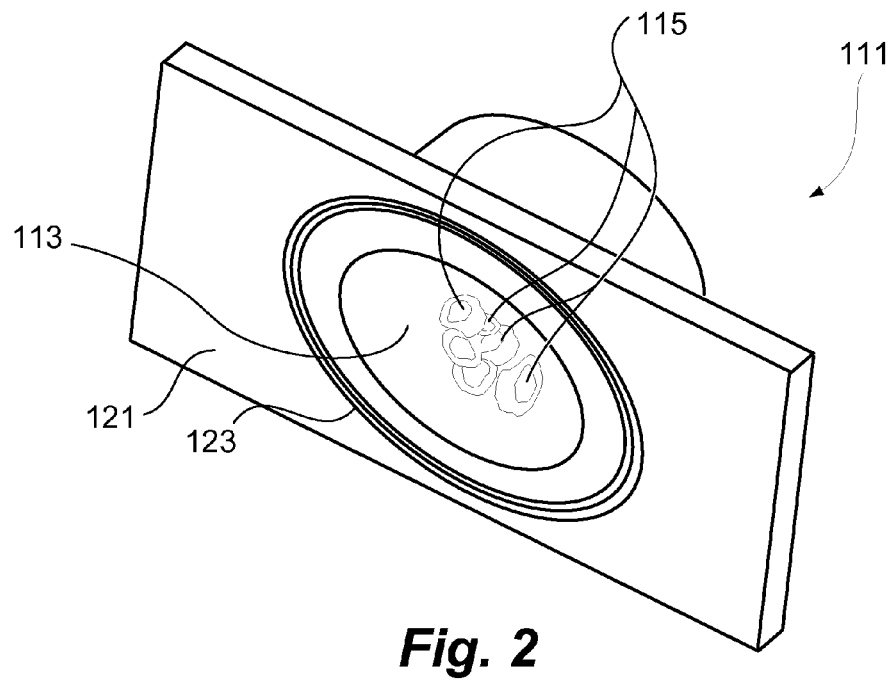
FIG. 2 is a back view of the shutter of FIG. 1, without a perforated cover, showing biocide crystals in a well portion.
Figure 3:
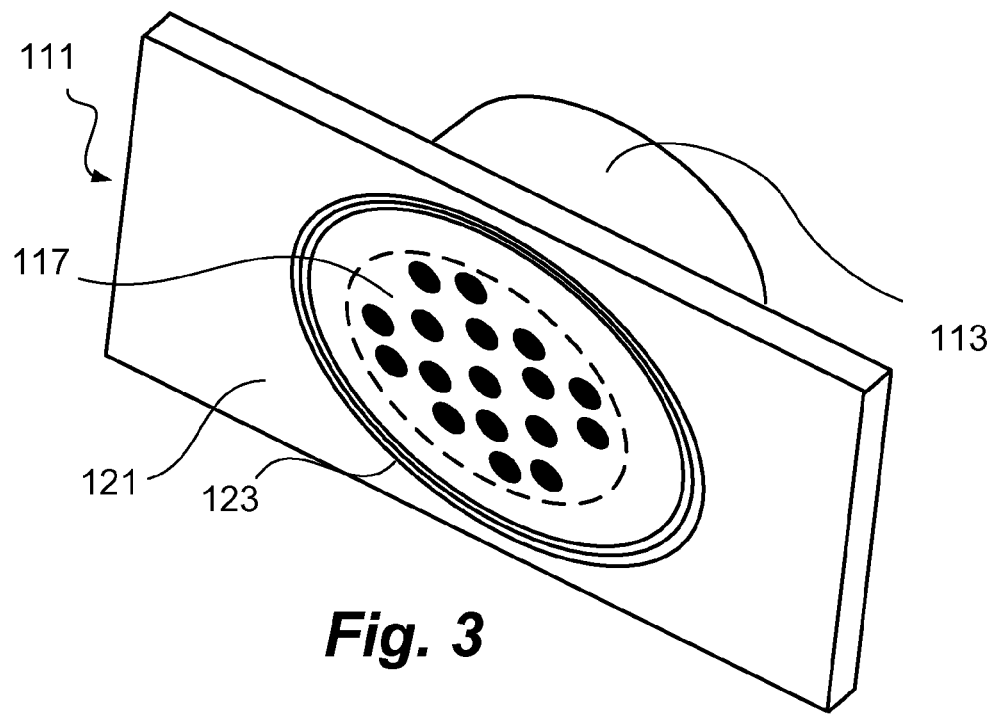
FIG. 3 is a back view of the shutter of FIGS. 1 and 2, showing the perforated cover.

FIGS. 1-3 are diagrams of an example construction of a shutter 111, implementing the disclosed techniques. FIG. 1 is a top perspective view, showing the outside of a well or reservoir 113, which serves as a chamber used for holding iodine crystals. FIG. 2 is a bottom perspective view of shutter 111, showing iodine crystals 115 in well 113. The arrangement comprises shutter 111 with well 113 to hold iodine crystals 115, and a screen or perforated surface 117, shown in FIG. 3. The perforated surface 117 is used to keep the iodine crystals 115 captive while allowing water to enter and dissolve some of the iodine from the crystals 115.

The shutter 111 is referred to as being mounted "semi-sealingly" in that the amount of fluid flow between the well or reservoir 113 and the sea or other aqueous environment is limited when the shutter 111 is closed, but such fluid flow is possible. The shutter 111 is mounted such that the volume encompassing the well or reservoir 113 and a sensor element 119 is not sealingly isolated from the ambient environment; rather, the small gap 120 between a facing surface 121 of shutter 111 and a surrounding mounting surface 122 (FIG. 1) of the sensor acts to limit the amount of flow of fluid occurring between the volume encompassing the reservoir 113 and the space in front of the sensor element 119.

In the closed state, the shutter 111 engages the sensor element 119 in order to retain the iodine in solution in contact with the sensor element 119. In order to do this, the shutter 111 engages a portion of the sensor element 119 or surrounding mounting surface 122 adjacent the sensor element 119 in order for the sensor element 119 to be protected in a semi-sealing manner. The portion of the sensor element 119 or surrounding mounting surface 122 adjacent the sensor thereby forms a mating surface for the shutter 111.

The semi-sealing manner is intended to describe a circumstance in which the concentration of iodine in water held between the sensor element 119 and the shutter 111 is maintained sufficiently to substantially prevent the iodine from being dissolved from the crystals 115 by action of the water flushing out the solution when the shutter 111 is closed. It is presumed that a substantial portion of the solution will be lost during active operational periods of the sensor element 119 when the shutter 111 is not engaging the sensor element 119, in which case, the iodine from the crystals 115 would again reach an equilibrium solution once the shutter 111 closes against the subject portion of the sensor element 119 or surrounding mounting surface 122.

In that manner, the iodine from the crystals 115 is permitted to diffuse into the surrounding water, although most of this loss will occur at times when the shutter 111 is opened. While a semi-sealing relationship is described, it is expected that in some applications, a substantially sealed relationship will be effected between the shutter 111 and its mating surface on the sensor element 119 or surrounding mounting surface 122 adjacent the sensor element 119. It is also expected that the shutter 111 may be configured to seal against a secondary mating surface (not shown) without covering the sensor element 119 when the shutter 111 is opened, thereby reducing iodine loss when the sensor element 119 is in operation. The secondary mating surface may be part of a housing for the sensor element 119 or may be a separate surface.

In one configuration, shown in FIG. 2, flat facing surface 121 is provided with a labyrinth seal 123. Labyrinth seal 123 is used to maintain a semi-sealing relationship between the shutter 111 and a sensor's surrounding mounting surface (122, FIG. 1). In this manner, the shutter 111 can retain the iodine in an effective concentration against a subject portion of the sensor element 119 between active operational periods of the sensor.

In the configuration shown in FIG. 2, the shutter 111 and sensor's surrounding mounting surface 122 are constructed such that when the shutter 111 is closed, there is a labyrinth type seal which hydraulically couples and prevents the free exchange of biocide saturated fluid with the ambient fluid.

It is also possible to construct the shutter 111 without the use of a separate seal, using the flat surface 121 to achieve a semi-sealing engagement with its mating surface 122. It is also expected that surface 121 may be formed to conform to the mating surface 122 which may not be flat. The flat surface 121 and the seal 123 may be made of a number of different materials, including metal, a polytetrafluoroethylene (PTFE) film, or any other suitable material. Alternatives include different shutter materials, considering characteristics such as strength, durability, and resistance to corrosion. Phenolic plastics have been considered and may be used, as they have good strength and toughness, and good resistance to solvents.

The technique is advantageous when used for long-term deployments, with intermittent data events. The shutter 111 is designed to cover a sensor element 119 with a small space 120 between the two. As described above, reservoir 113 containing iodine crystals 115 is covered with perforated surface 117 that faces the sensor element 119. Perforated surface 117 is intended to keep the crystals 115 captive while allowing the iodine to saturate what should be a fairly static amount of water.

As the sensor element 119 is deployed, water will seep into the space between sensor element 119 and shutter 111. During deployment, including at times when a biofilm would be likely to form, the water saturates with dissolved iodine, preventing the biofilm from forming in the first place. The minimal exchange of water through the space results in the constant presence of a saturated iodine solution, providing constant protection. Should some of the solution be flushed out and replaced with new water, the remaining iodine crystals 115 will dissolve until the solution reaches saturation.

During a data event, the shutter 111 opens briefly. Once the event is complete, the shutter 111 closes, containing a fresh volume of water at which point the saturation process begins again.

Crystallized iodine, which form crystals 115, is well-suited for this use due to its low solubility. It takes very little dissolved iodine to saturate a volume of water; therefore the crystals 115 can last for a long-term deployment.

The low solubility of iodine and availability of the crystalline form makes iodine a suitable biocide for this system, as it takes only a small amount to saturate the water while the rest remains in its crystalline form. The capacity of iodine to last a long time allows for a long-term deployment.

Finally, iodine has the advantage of a lower environmental impact than other biocides in use, such as cuprous oxide, tributyltin (TBT) and Irgarol 1051. Iodine is a powerful oxidizer, toxic to living organisms in high doses but is also naturally-occurring in seawater in low concentrations. It does not bio-accumulate in the food chain like other biocides (e.g., lead, copper, mercury, TBT, Irgarol), and is actually an essential mineral for thyroid function in warm-blooded animals. Though it is toxic in large amounts, it is unlikely it will be released into the environment at harmful levels. Iodine is a naturally occurring element in seawater (about 0.0003 ppm), which is the primary source for commercial iodine production.

The biocide should dissolve rapidly enough for the biocide to become effective quickly enough to control microbial growth when the shutter is closed sufficiently. The biocide should also have longevity while in service, for example by reaching saturation as a solute when the shutter 111 is closed and dissolving slowly when the shutter 111 is opened.

One option in constructing the shutter 111 includes coating the outside of the shutter (the part not facing against or juxtaposed with the sensor element 119) with a thin layer of copper. This would deter fouling in the vicinity of the sensor/shutter assembly and reduce the likelihood of malfunction of moving parts.

The configuration in which perforated surface 117 is flush with flat surface 121 is suitable for use with sensors which are recessed from their mounting surface. It is expected that the technique will be used with sensors which are not recessed, in which case, the shutter 111 should clear the sensor element 119. In the configuration depicted in FIG. 4, a shutter 411 is constructed, so a facing surface 421 of the shutter is flat and may include a seal 423. In the case of a flat sensor element 119, the small space 425 forming a recess between sensor element 119 and shutter is built into the shutter by providing screen or perforated surface 427 as recessed from facing surface 421. Perforated surface 427 forms a barricade between the solid iodine crystals (not shown) and the sensor element 119 in order to retain the crystals in the shutter 411 and is set back behind the plane of the facing surface 421 to define the recess 425.

The mounting surface 122 onto which the shutter 111 is mounted is of course dependent on the sensor element 119 installation. FIG. 5 is a diagram showing a non-limiting exemplary sensor element 119 mounting plate 501 having a curved outer mounting surface 505. The sensor mounting plate 501 is provided with multiple sensor openings 507 supporting sensor elements 119, two of which are depicted uncovered and two of which are depicted covered by shutters 511. Shutters 511 can either be flat to seal against the mating sensor opening (507) or have mounting plates 519 which conform to curved surface 505. In that manner, the facing surface (e.g., facing surface 421, FIG. 4) conforms to mounting plate 501 and uses outer surface 505 as a mating surface.

If desired, mounting surface 505 may be faced (the surface mechanically prepared) with a desired finish. This permits the mounting surface 505 to conform to the shutters 511 as desired to achieve a sealing relationship with the shutters 511 or alternatively to achieve a semi-sealing relationship with the shutters 511, achieved by a gap 521 between the shutters 511 and the mounting surface 505.

Figure 4:
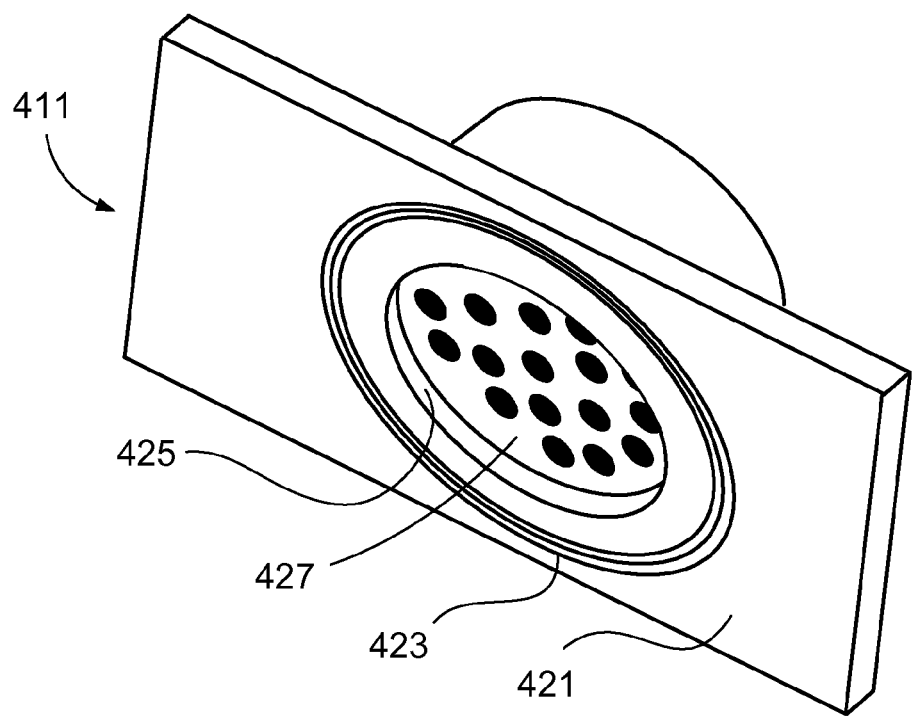
FIG. 4 is a back view of an alternate configuration of the shutter, in which a recess is provided.
Figure 5:
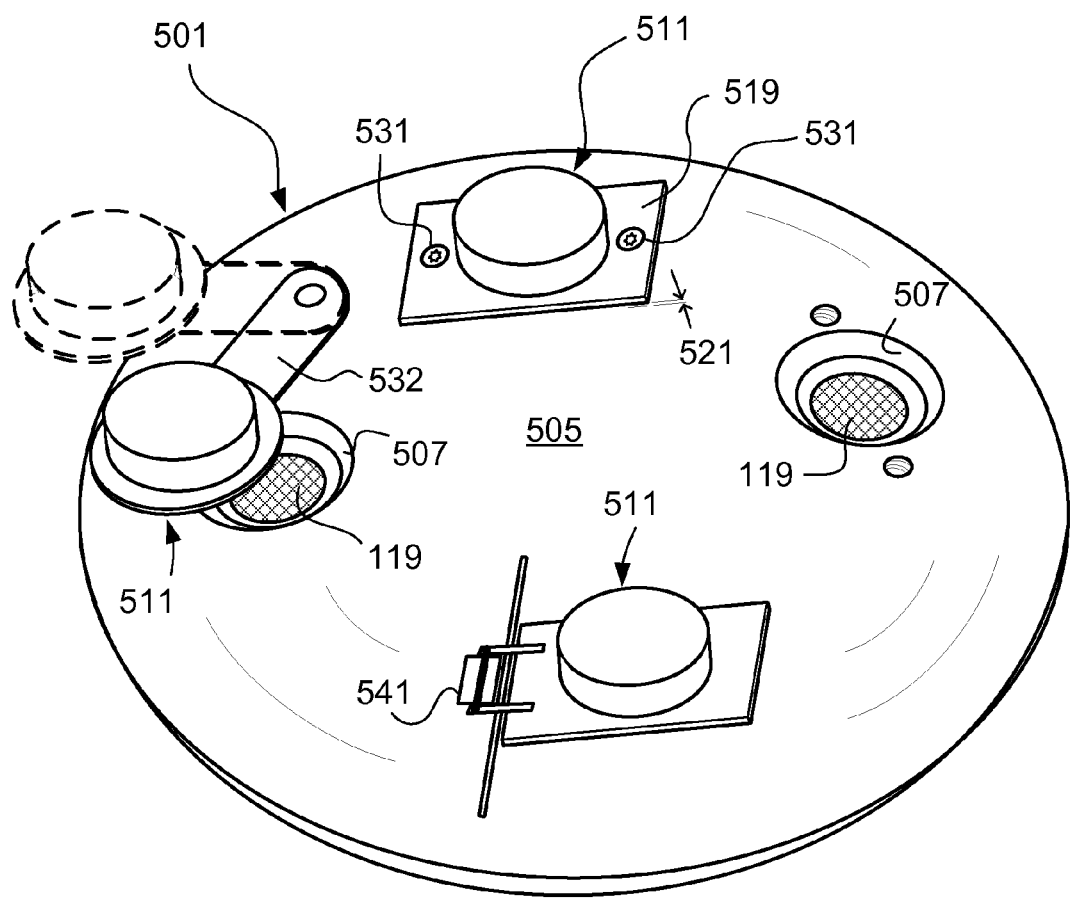
FIG. 5 is a diagram showing shutters on a sensor element mounting plate.

The gap 521 between the sensor element 119 or the sensor's surrounding mounting surface 505 and the shutter 511 is in the range of 0.05 mm, with possible ranges varying greatly depending on the construction of the labyrinth seal 123 or 423 (FIGS. 2-4). Other ranges include 0.1 mm to 0.01 mm, or 0.5 mm to 0.002 mm. It is also possible to provide a substantially watertight seal, or a substantially watertight seal with a leakage passage accommodating variations in pressure.

In a test configuration, shutters 511 were mounted with fasteners 531; however, it is expected that an automatic mechanism such as actuator or servo 541 will be used to control shutters 511 without the need for manual operation. It is also possible to couple the shutter 511 to a rotational arm 532, which may be coupled to a servo (not shown) mounted beneath the mounting surface 505.

It will be understood that many additional changes in the details, materials, steps and arrangement of parts, which have been herein described and illustrated to explain the nature of the invention, may be made by those skilled in the art within the principle and scope of the invention as expressed in the appended claims.

What is claimed is:

1. Apparatus for protecting a sensor in an aqueous environment, the apparatus comprising:
    a shutter having a facing surface and a reservoir, the shutter configured to cover a mating surface comprised of a subject portion of the sensor or surrounding mounting surface adjacent the sensor in at least a semi-sealing manner; and
    the reservoir having a capability of holding a biocide having a limited water solubility and a low environmental toxicity in the aqueous environment, the reservoir in communication with the mating surface while positioned against the mating surface, wherein the reservoir is fixed to an opening in the facing surface to form a well for holding the biocide, wherein the shutter further comprises a screen for retaining the biocide within the well, and wherein the screen has a recessed alignment with respect to the facing surface.

2. Apparatus for protecting a sensor as described in claim 1, wherein the biocide comprises iodine in solid form.

3. Apparatus for protecting a sensor as described in claim 1, wherein the biocide comprises anhydrous iodine crystals.

4. Apparatus for protecting a sensor as described in claim 1, wherein the shutter comprises:
    a labyrinth seal on the facing surface capable of establishing a semi-sealing relationship with the mating surface.

5. Apparatus for protecting a sensor as described in claim 1, wherein the shutter comprises:
    a facing surface for conforming with a mating surface supporting the sensor;
    a polytetrafluoroethylene (PTFE) film on the facing surface, establishing a semi-sealing relationship between the shutter and the mating surface.

6. Apparatus for protecting a sensor as described in claim 1, wherein the shutter comprises:
    a layer of copper on at least one surface of the shutter.

7. Apparatus for protecting a sensor as described in claim 1, wherein the shutter comprises:
    a layer of copper on at least one surface of the shutter not facing against the sensor.

* * * * *